US00RE49542E

(19) United States
(12) Reissued Patent
Stroun et al.

(10) Patent Number: US RE49,542 E
(45) Date of Reissued Patent: Jun. 6, 2023

(54) METHOD FOR THE DETECTION OF CANCER

(71) Applicant: Guardant Health, Inc., Redwood City, CA (US)

(72) Inventors: Maurice Stroun, Geneva (CH); Philippe Anker, Geneva (CH)

(73) Assignee: Guardant Health, Inc., Palo Alto, CA (US)

(21) Appl. No.: 14/039,168

(22) Filed: Sep. 27, 2013

Related U.S. Patent Documents

Reissue of:
(64) Patent No.: 7,700,286
Issued: Apr. 20, 2010
Appl. No.: 11/336,780
Filed: Jan. 23, 2006

U.S. Applications:
(62) Division of application No. 13/447,104, filed on Apr. 13, 2012, now Pat. No. Re. 44,596, which is an application for the reissue of Pat. No. 7,700,286.

(30) Foreign Application Priority Data

Apr. 6, 2005 (EP) ..... 05007508

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/16* (2013.01)

(58) Field of Classification Search
CPC ..... C12Q 1/6886
See application file for complete search history.

(56) References Cited

U.S. PATENT DOCUMENTS 5,496,699 A 3/1996 Sorenson
5,569,753 A 10/1996 Wigler et al.
5,602,243 A 2/1997 Vogelstein
5,648,245 A 7/1997 Fire et al.
5,952,170 A 9/1999 Stroun et al.
6,329,179 B1 12/2001 Kopreski
6,492,121 B2 12/2002 Kurane et al.
6,586,177 B1 7/2003 Shuber
6,664,046 B1 12/2003 Chang et al.
6,849,403 B1 2/2005 Shuber
6,916,634 B2 7/2005 Kopreski
6,939,671 B2 9/2005 Kopreski
7,163,789 B2 1/2007 Chen et al.
7,208,275 B2 4/2007 Gocke et al.
7,282,335 B2 * 10/2007 Gocke ..... C07K 14/47 435/6.11
7,410,764 B2 8/2008 Gocke et al.
7,700,286 B2 4/2010 Stroun et al.
7,767,423 B2 8/2010 Kopreski
7,785,842 B2 8/2010 Kopreski
7,824,889 B2 11/2010 Vogelstein et al.
7,888,008 B2 * 2/2011 Sozzi ..... 435/6.12
7,915,015 B2 3/2011 Vogelstein et al.
7,935,487 B2 5/2011 Gocke et al.
7,937,225 B2 5/2011 Mishra et al.
RE44,596 E 11/2013 Stroun et al.
8,603,749 B2 12/2013 Gillevet
8,685,678 B2 4/2014 Casbon et al.
9,404,156 B2 8/2016 Hicks et al.
2002/0072058 A1 6/2002 Voelker et al.
2003/0166914 A1 * 9/2003 Ni et al. ..... 536/23.5
2004/0259101 A1 * 12/2004 Shuber ..... C12Q 1/6886 435/6.18
2005/0095592 A1 * 5/2005 Jazaeri et al. ..... 435/6
2006/0073506 A1 4/2006 Christians et al.
2007/0065823 A1 3/2007 Dressman et al.
2007/0092874 A1 * 4/2007 Hsiao et al. ..... 435/6
2008/0161420 A1 7/2008 Shuber
2009/0087847 A1 4/2009 Lo et al.
2009/0105959 A1 4/2009 Braverman et al.
2010/0041048 A1 2/2010 Diehl et al.
2010/0069250 A1 3/2010 White, III et al.
2010/0323348 A1 12/2010 Hamady et al.
2011/0177512 A1 7/2011 Shuber
2011/0201507 A1 8/2011 Rava et al.
(Continued)

FOREIGN PATENT DOCUMENTS

CA 2731991 A1 2/2010
EP 1 158 055 11/2001
(Continued)

OTHER PUBLICATIONS

Sozzi et al. (J. of Clini. Oncology, vol. 21, No. 21, pp. 3902-3908, Nov. 2003).*
Applied Bio systems (AB) User Bulletin #2 (Updated Oct. 2001).*
Tricarico et al. (Analytical Biochemistry, vol. 309, pp. 293-300, 2002).*
Bernard et al. (Clinical Chemistry, vol. 48, No. 8, pp. 1178-1185, 2002).*
Wellmann et al. (Clinical Chemistry, vol. 47, No. 4, pp. 654-660, 2001).*
Koesters et al. (Koesters) Cancer Research, 59:3880-82, 1999.*
Millson et al., (Millson) J. Mol. Diag. 5(3):184-190, 2003.*
Khan et al., Int. J. Cancer 110:891-895, 2004.*
(Continued)

*Primary Examiner* — Sharon Turner
(74) *Attorney, Agent, or Firm* — Wilson Sonsini Goodrich & Rosati

(57) ABSTRACT

The present invention relates to a method for the diagnosis and/or the follow up of the evolution of cancer, which includes the analysis and quantification of over expressed and amplified genes in the plasma/serum of cancer patients or persons suspected to harbor cancer. This is achieved by analyzing together the amount of DNA and RNA of certain genes in the plasma/serum of cancer patients that are the reflection of a gene amplification and/or a gene over expression in comparison to healthy controls.

18 Claims, 3 Drawing Sheets

Specification includes a Sequence Listing.

(56) References Cited

U.S. PATENT DOCUMENTS

| | | | |
|---|---|---|---|
| 2011/0264376 | A1 | 10/2011 | Chinitz et al. |
| 2012/0003637 | A1 | 1/2012 | Lo et al. |
| 2012/0094849 | A1 | 4/2012 | Rava et al. |
| 2012/0100548 | A1 | 4/2012 | Rava et al. |
| 2012/0149582 | A1 | 6/2012 | Rava et al. |
| 2012/0165203 | A1 | 6/2012 | Quake et al. |
| 2012/0316074 | A1 | 12/2012 | Saxonov |
| 2013/0005585 | A1 | 1/2013 | Anderson et al. |
| 2013/0022977 | A1 | 1/2013 | Lapidus et al. |
| 2013/0210643 | A1 | 8/2013 | Casbon et al. |
| 2013/0224743 | A1 | 8/2013 | Casbon et al. |
| 2013/0237458 | A1 | 9/2013 | Casbon et al. |
| 2013/0267424 | A1 | 10/2013 | Casbon et al. |

FOREIGN PATENT DOCUMENTS

| | | | |
|---|---|---|---|
| EP | 1158055 | A1 | 11/2001 |
| EP | 1647600 | A2 | 4/2006 |
| WO | WO 93/22456 | A1 | 11/1993 |
| WO | WO 97/35589 | | 10/1997 |
| WO | WO 97/35589 | A1 | 10/1997 |
| WO | WO-9941406 | A1 | 8/1999 |
| WO | WO-0058516 | A2 | 10/2000 |
| WO | WO 01/90409 | | 11/2001 |
| WO | WO 01/90409 | A1 | 11/2001 |
| WO | WO-0218652 | A2 | 3/2002 |
| WO | WO 2007/050465 | A2 | 5/2007 |
| WO | WO-2012014877 | A1 | 2/2012 |
| WO | WO 2012/028746 | A1 | 3/2012 |
| WO | WO-2013019075 | A2 | 2/2013 |

OTHER PUBLICATIONS

Lo et al., Quantitative Analysis of Cell-free Epstein-Barr Virus DNA in Plasma of Patients with Nasopharyngeal Carcinoma, Cancer Research 59:1188-1191, Mar. 15, 1999.*

Mutirangura et al., (Mutirangura), Epstein-Barr Viral DNA in Serum of Patients with Nasopharyngeal Carcinoma, Clinical Cancer Res., 4:665-659, Mar. 1998.*

Lo et al., (Lo Nov. 1999), Quantitative and Temporal Correlation between Circulating Cell-Free Epstein-Barr Virus DNA and Tumor Recurrence in Nasopharyngeal Carcinoma, Cancer Research 59:5452-5455, Nov. 1, 1999.*

Dasi et al., Real-Time Quantification in Plasma of Human Telomerase Reverse Transcriptase (hTERT) mRNA: A simple Blood Test to Monitor Disease in Cancer Patients, Laboratory Investigation 81(5):767-769, May 2001.*

Anker, et al. Circulating nucleic acids in plasma and serum as a noninvasive investigation for cancer: time for large-scale clinical studies? Int J Cancer. Jan. 10, 2003;103(2):149-52.

Anker, et al. Detection of circulating tumour DNA in the blood (plasma/serum) of cancer patients. Cancer Metastasis Rev. 1999;18(1):65-73.

Anker, et al. Progress in the knowledge of circulating nucleic acids: plasma RNA is particle-associated. Can it become a general detection marker for a cancer blood test? Clin Chem. Aug. 2002;48(8):1210-1.

Chan, et al. Plasma Epstein-Barr virus DNA and residual disease after radiotherapy for undifferentiated nasopharyngeal carcinoma. J Natl Cancer Inst. Nov. 6, 2002;94(21):1614-9.

Chen, et al. Telomerase RNA as a detection marker in the serum of breast cancer patients. Clin Cancer Res. Oct. 2000;6(10):3823-6.

Dasi, et al. Real-time quantification in plasma of human telomerase reverse transcriptase (hTERT) mRNA: a simple blood test to monitor disease in cancer patients. Lab Invest. May 2001;81(5):767-9.

European search report and opinion dated Aug. 26, 2005 for EP Application No. 05007508.4.

Fleischhacker, et al. Detection of amplifiable messenger RNA in the serum of patients with lung cancer. Ann N Y Acad Sci. Sep. 2001;945:179-88.

Goessl. Diagnostic potential of circulating nucleic acids for oncology. Expert Rev Mol Diagn. Jul. 2003;3(4):431-42.

Hasselmann, et al. Detection of tumor-associated circulating mRNA in serum, plasma and blood cells from patients with disseminated malignant melanoma. Oncol Rep. Jan.-Feb. 2001;8(1):115-8.

Kopreski, et al. Detection of tumor messenger RNA in the serum of patients with malignant melanoma. Clin Cancer Res. Aug. 1999;5(8):1961-5.

Nawroz, et al. Microsatellite alterations in serum DNA of head and neck cancer patients. Nat Med. Sep. 1996;2(9):1035-7.

Office Action dated May 16, 2013 for U.S. Appl. No. 13/447,104.

Office Action dated Jul. 7, 2009 for U.S. Appl. No. 11/336,780.

Office Action dated Sep. 18, 2012 for U.S. Appl. No. 13/447,104.

Rykova, et al. Breast cancer diagnostics based on extracellular DNA and RNA circulating in blood. Biochemistry (Moscow) Supplement Series B: Biomedical Chemistry. 2008; 2(2):208-213.

Silva, et al. Detection of epithelial messenger RNA in the plasma of breast cancer patients is associated with poor prognosis tumor characteristics. Clin Cancer Res. Sep. 2001;7(9):2821-5.

Silva, et al. Detection of epithelial tumour RNA in the plasma of colon cancer patients is associated with advanced stages and circulating tumour cells. Gut. Apr. 2002;50(4):530-4.

Silva, et al. RNA is more sensitive than DNA in identification of breast cancer patients bearing tumor nucleic acids in plasma. Genes Chromosomes Cancer. Dec. 2002;35(4):375-6.

Wong, et al. New markers for cancer detection. Curr Oncol Rep. Nov. 2002;4(6):471-7.

Wong, et al. Quantitative correlation of cytokeratin 19 mRNA level in peripheral blood with disease stage and metastasis in breast cancer patients: potential prognostic implications. Int J Oncol. Mar. 2001;18(3):633-8.

Wong, et al. Quantitative relationship of the circulating tumor burden assessed by reverse transcription-polymerase chain reaction for cytokeratin 19 mRNA in peripheral blood of colorectal cancer patients with Dukes' stage, serum carcinoembryonic antigen level and tumor progression. Cancer Lett. Jan. 10, 2001;162(1):65-73.

Diehl, et al. Circulating mutant DNA to assess tumor dynamics. Nat Med. Sep. 2008;14(9):985-90. doi: 10.1038/nm.1789. Epub Jul. 31, 2007.

Diehl, et al. Detection and quantification of mutations in the plasma of patients with colorectal tumors. Proc Natl Acad Sci U S A. Nov. 8, 2005;102(45):16368-73. Epub Oct. 28, 2005.

Fredriksson, et al. Multiplex amplification of all coding sequences within 10 cancer genes by Gene-Collector. Nucleic Acids Res. 2007;35(7):e47. Epub Feb. 22, 2007.

Shinozaki, et al. Utility of circulating B-RAF DNA mutation in serum for monitoring melanoma patients receiving biochemotherapy. Clin Cancer Res. Apr. 1, 2007;13(7):2068-74.

Notice of allowance dated Jul. 22, 2013 for U.S. Appl. No. 13/447,104.

Notice of allowance dated Dec. 8, 2009 for U.S. Appl. No. 11/336,780.

Alkan, et al. Personalized copy number and segmental duplication maps using next-generation sequencing. Nat Genet. Oct. 2009;41(10):1061-7. doi: 10.1038/ng.437. Epub Aug. 30, 2009.

Atanur, et al. The genome sequence of the spontaneously hypertensive rat: Analysis and functional significance. Genome Res. Jun. 2010;20(6):791-803. doi: 10.1101/gr.103499.109. Epub Apr. 29, 2010.

Bonaldo, et al. Normalization and subtraction: two approaches to facilitate gene discovery. Genome Res. Sep. 1996;6(9):791-806.

Carr, et al. Inferring relative proportions of DNA variants from sequencing electropherograms. Bioinformatics. Dec. 15, 2009;25(24):3244-50. doi: 10.1093/bioinformatics/btp583. Epub Oct. 9, 2009.

Castle, et al. DNA copy number, including telomeres and mitochondria, assayed using next-generation sequencing. BMC Genomics. Apr. 16, 2010;11:244. doi: 10.1186/1471-2164-11-244.

Chang, et al. Detection of allelic imbalance in ascitic supernatant by digital single nucleotide polymorphism analysis. Clin Cancer Res. Aug. 2002;8(8):2580-5.

Costello, et al. Discovery and characterization of artifactual mutations in deep coverage targeted capture sequencing data due to

(56) References Cited

OTHER PUBLICATIONS oxidative DNA damage during sample preparation. Nucleic Acids Res. Apr. 1, 2013;41(6):e67. doi: 10.1093/nar/gks1443. Epub Jan. 8, 2013.
Daines, et al. High-throughput multiplex sequencing to discover copy number variants in Drosophila. Genetics. Aug. 2009;182(4):935-41. doi: 10.1534/genetics.109.103218. Epub Jun. 15, 2009.
Fan, et al. Non-invasive prenatal measurement of the fetal genome. Nature. Jul. 19, 2012;487(7407):320-4. doi: 10.1038/nature11251.
Grant, et al. SNP genotyping on a genome-wide amplified DOP-PCR template. Nucleic Acids Res. Nov. 15, 2002;30(22):e125.
Gundry, et al. Direct, genome-wide assessment of DNA mutations in single cells. Nucleic Acids Res. Mar. 2012;40(5):2032-40. doi: 10.1093/nar/gkr949. Epub Nov. 15, 2011.
Gundry, et al. Direct mutation analysis by high-throughput sequencing: from germline to low-abundant, somatic variants. Mutat Res. Jan. 3, 2012;729(1-2):1-15. doi: 10.1016/mrfmmm.2011.10.001. Epub Oct. 12, 2011.
Hamady, et al. Error-correcting barcoded primers for pyrosequencing hundreds of samples in multiplex. Nat Methods. Mar. 2008;5(3):235-7. doi: 10.1038/nmeth.1184. Epub Feb. 10, 2008.
Hensel, et al. Simultaneous identification of bacterial virulence genes by negative selection. Science. Jul. 21, 1995;269(5222):400-3.
Hiatt, et al. Single molecule molecular inversion probes for targeted, high-accuracy detection of low-frequency variation. Genome Res. May 2013;23(5):843-54. doi: 10.1101/gr147686.112. Epub Feb. 4, 2013.
Lizardi, et al. Mutation detection and single-molecule counting using isothermal rolling-circle amplification. Nat Genet. Jul. 1998;19(3):225-32.
Makrigiorgos, et al., A PCR-Based amplification method retaining quantative difference between two complex genomes. Nature Biotech, vol. 20, No. 9, pp. 936-939 (Sep. 2002).
Medvedev, et al. Detecting copy number variation with mated short reads. Genome Res. Nov. 2010;20(11):1613-22. doi: 10.1101/gr.106344.110. Epub Aug. 30, 2010.
Mei, et al. Identification of recurrent regions of Copy-Number Variants across multiple individuals. BMC Bioinformatics. Mar. 22, 2010;11:147. doi: 10.1186/1471-2105-11-147.
Ogino, et al. Quantification of PCR bias caused by a single nucleotide polymorphism in SMN gene dosage analysis. J Mol Diagn. Nov. 2002;4(4):185-90.
Park, et al. Discovery of common Asian copy number variants using integrated high-resolution array CGH and massively parallel DNA sequencing. Nat Genet. May 2010;42(5):400-5. doi: 10.1038/ng.555. Epub Apr. 4, 2010.
Pleasance, et al. A small-cell lung cancer genome with complex signatures of tobacco exposure. Nature. Jan. 14, 2010;463(7278):184-90. doi: 10.1038/nature08629. Epub Dec. 16, 2009.
Simpson, et al. Copy number variant detection in inbred strains from short read sequence data. Bioinformatics. Feb. 15, 2010;26(4):565-7. doi: 10.1093/bioinformatics/btp693. Epub Dec. 18, 2009.
Tan, et al. Genome-wide comparison of DNA hydroxymethylation in mouse embryonic stem cells and neural progenitor cells by a new comparative hMeDIP-seq method. Nucleic Acids Res. Apr. 2013;41(7):e84. doi: 10.1093/nar/gkt091. Epub Feb. 13, 2013.
Taudien, et al. Haplotyping and copy number estimation of the highly polymorphic human beta-defensin locus on 8p23 by 454 amplicon sequencing. BMC Genomics. Apr. 19, 2010:11:252. doi: 10.1186/1471-2164-11-252.
Tomaz, et al. Differential methylation as a cause of allele dropout at the imprinted GNAS locus. Genet Test Mol Biomarkers. Aug. 2010;14(4):455-60. doi: 10.1089/gtmb.2010.0029.
Walker, et al. Isothermal in vitro amplification of DNA by a restriction enzyme/DNA polymerase system. Proc Natl Acad Sci USA. Jan. 1, 1992;89(1):392-6.
Walsh, et al. Detection of inherited mutations for breast and ovarian cancer using genomic capture and massively parallel sequencing. Proc Natl Acad Sci U S A. Jul. 13, 2010;107(28):12629-33. doi: 10.1073/pnas.1007983107. Epub Jun. 28, 2010.
Weber, et al. A real-time polymerase chain reaction assay for quantification of allele ratios and correction of amplification bias. Anal Biochem. Sep. 15, 2003;320(2):252-8.
Wojdacs, et al. Primer design versus PCR bias in methylation independent PCR amplifications. Epigenetics. May 16, 2009;4(4):231-4. Epub May 14, 2009.
Wood, et al. Using next-generation sequencing for high resolution multiplex analysis of copy number variation from nanogram quantities of DNA from formalin-fixed paraffin-embedded specimens. Nucleic Acids Res. Aug. 2010;38(14):e151. doi: 10.1093/nar/gkq510. Epub Jun. 4, 2010.
Yandell, et al. A probabilistic disease-gene finder for personal genomes. Genome Res. Sep. 2011;21(9):1529-42. doi: 10.1101/gr.123158.111. Epub Jun. 23, 2011.
Yoon, et al. Sensitive and accurate detection of copy number variants using read depth of coverage. Genome Res. Sep. 2009;19(9):1586-92. doi: 10.1101/gr.092981.109. Epub Aug. 5, 2009.
Zhang, et al. The impact of next-generation sequencing on genomics. J Genet Genomics. Mar. 20, 2011;38(3):95-109. doi: 10.1016/j.jgg.2011.02.003. Epub Mar. 15, 2011.
Allard, et al. Tumor cells circulate in the peripheral blood of all major carcinomas but not in healthy subjects or patients with nonmalignant diseases. Clin Cancer Res. Oct. 15, 2004;10(20):6897-904.
Benohr, et al. Her-2/neu expression in breast cancer—A comparison of different diagnostic methods. Anticancer Res. May-Jun. 2005;25(3B):1895-900.
Beyser, et al. Real-time Quantification of HER2/neu Gene Amplification by LightCycler Polymerase Chain Reaction (PCR)—a New Research Tool. Biochemica. 2001;2:15-8.
Cardoso, et al. Genomic profiling by DNA amplification of laser capture microdissected tissues and array CGH. Nucleic Acids Res. Oct. 28, 2004;32(19):e146.
Dulaimi, et al. Tumor suppressor gene promoter hypermethylation in serum of breast cancer patients. Clin Cancer Res. Sep. 15, 2004;10(18 Pt 1):6189-93.
FDA Approval Letter. Reference No. 98-0369. Dated Sep. 25, 1998. 3 pgs.
Gjerdrum, et al. Real-time quantitative PCR of microdissected paraffin-embedded breast carcinoma: an alternative method for HER-2/neu analysis. J Mol Diagn. Feb. 2004;6(1):42-51.
Hunt, et al. Microdissection techniques for molecular testing in surgical pathology. Arch Pathol Lab Med. Dec. 2004;128(12):1372-8.
Krainer, et al. Tissue expression and serum levels of HER-2/neu in patients with breast cancer. Oncology. Nov.-Dec. 1997;54(6):475-81.
Naber, et al. Strategies for the analysis of oncogene overexpression. Studies of the neu oncogene in breast carcinoma. Am J Clin Pathol. Aug. 1990;94(2):125-36.
Pinkel, et al. High resolution analysis of DNA copy number variation using comparative genomic hybridization to microarrays. Nat Genet. Oct. 1998;20(2):207-11.
Risinger, et al. Microarray analysis reveals distinct gene expression profiles among different histologic types of endometrial cancer. Cancer Res. Jan. 1, 2003;63(1):6-11.
Ross, et al. The Her-2/neu gene and protein in breast cancer 2003: biomarker and target of therapy. Oncologist. 2003;8(4):307-25.
Schaller, et al. Current use of HER2 tests. Ann Oncol. 2001;12 Suppl 1:S97-100.
Schwarzenbach, et al. Detection and characterization of circulating microsatellite-DNA in blood of patients with breast cancer. Ann N Y Acad Sci. Jun. 2004;1022:25-32.
Shaw, et al. Microsatellite alterations plasma DNA of primary breast cancer patients. Clin Cancer Res. Mar. 2000;6(3):1119-24.
Silva, et al. TP53 gene mutations in plasma DNA of cancer patients. Genes Chromosomes Cancer. Feb. 1999;24(2): 160-1.
Slamon, et al. Human breast cancer: correlation of relapse and survival with amplification of the HER-2/neu oncogene. Science. Jan. 9, 1987;235(4785):177-82.

(56) References Cited

OTHER PUBLICATIONS

Sorenson, et al. Soluble normal and mutated DNA sequences from single-copy genes in human blood. Cancer Epidemiol Biomarkers Prev. Jan.-Feb. 1994;3(1):67-71.
Suo, et al. Real-time PCR quantification of c-erbB-2 gene is an alternative for FISH in the clinical management of breast carcinoma patients. Int J Surg Pathol. Oct. 2004;12(4):311-8.
Vasioukhin, et al. Point mutations of the N-ras gene in the blood plasma DNA of patients with myelodysplastic syndrome or acute myelogenous leukaemia. Br J Haematol. Apr. 1994;86(4):774-9.
Mutirangura, A. et al. "Esptein-Barr Viral DNA in Serum of Patients with Nasopharyngeal Carcinoma" Clin Canc Res (1998) 4:665-669.
Rykova et al., Biochemistry (Moscow) Supplement Series B: Biomedical Chemistry, vol. 2, 2008. pp. 208-213.*
Wong and Lo, Current Oncology Reports, 2002, vol. 4, pp. 471-477.*
Anker and Stroun, Clinical Chemistry, vol. 48, No. 8, 2002, pp. 1210-1211.*
Anker et al., Cancer and Metastasis Reviews, 1999, vol. 18, pp. 65-73.*
Silva et al., Genes, Chromosomes and Cancer, vol. 35, pp. 375-376, 2002.*
Philippe Anker et al., "Circulating Nucleic Acids in Plasma and Serum as a Noninvasive Investigation for Cancer: Time for Large-Scale Clinical Studies?", International Journal of Cancer, 2003, pp. 149-152, XP 002275956.
Carsten Goessl, "Diagnostic Potential of Circulating Nucleic Acids for Oncology", Expert Review of Molecular Diagnostics, 2003, vol. 3, No. 4, p. 431-442, XP009052512.
Javier Silva et al., "RNA is More Sensitive than DNA in Identification of Breast Cancer Patients Bearing Tumor Nucleic Acids in Plasma", Genes, Chromosomes & Cancer, vol. 35, No. 4, 2002, pp. 375-376, XP009052544.

* cited by examiner

METHOD FOR THE DETECTION OF CANCER

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*Notice: More than one reissue application has been filed for the reissue of U.S. Pat. No. 7,700,286, which claims the benefit of European Patent Application No. 05007508, which was filed on Apr. 6, 2005. This application is a reissue divisional of U.S. patent application Ser. No. 13,447,104, entitled "Methods for Detection of Cancer," filed on Apr. 13, 2012, which is an application for reissue of U.S. Pat. No. 7,700,286. The reissue applications are the present reissue divisional application and the parent reissue application Ser. No., 13/477,104, which issued as RE 44,596. The instant application adds new claims relative to the original patent, U.S. Pat. No. 7,700,286. The entire contents and disclosures of the above applications are hereby incorporated by reference.*

The present invention describes a method of diagnosis and/or follow up of the evolution of most types of cancer, for instance after a chemotherapy or after an operation.

It is known that diagnosis and follow up of the evolution of cancer are done, besides direct observation of the tumors, by biopsy analysis or in the case of blood malignancies by analysis of the bone marrow. This implies either a surgical intervention or an invasive test such as a biopsy or a bone marrow aspiration. Now, without taking into account the disagreeable or even dangerous aspect of such methods it has been observed that they could moreover not be very precise.

Conventional methods of diagnosis are not very satisfactory. As an example, colorectal cancer screening presently relies on fecal occult blood testing (FOBT) which is both insensitive and non-specific. In contrast, flexible sigmoidoscopy is sensitive and specific for early distal disease but is both invasive and insensitive for proximal disease. Furthermore, barium enema is relatively sensitive and specific but requires colonic preparation, radiation and a day off work, while total colonoscopy is highly sensitive and specific but is also invasive and expensive.

The situation appears little better for other cancers. No reliable test is available for early detection of lung cancer, with computerized tomography being the most reliable tool.

An important strategy to reduce mortality from breast cancer is the introduction of mammographic screening in an attempt to detect cancers at an asymptomatic and pathologically early stage. Although several studies indicate that mass screening is a useful strategy for reducing breast cancer mortality, there are a number of disadvantages associated with this form of cancer screening. These include a high rate of false positive tests, frequent false negative tests and the enormous public health costs involved. Thus, when the benefits of mammographic screening are weighed against its costs and other disadvantages, it is perhaps not surprising that this form of screening has engendered an enthusiastic and contentious debate over the past 20 years.

Finally, development of conventional protein tumor markers, such as carcinoembryonic antigen (CEA) and alpha-fetoprotein (AFP), along with the widely used prostate specific antigen (PSA) was driven largely by the introduction of new methods for quantifying small amounts of circulating proteins. However, sensitivity and specificity shortcomings with these assays remain to be overcome.

The aim of this invention consists therefore in providing a method of diagnosis and/or follow up of the evolution of most types of cancer which would be, on one hand, more precise and trustworthy and, on the other hand easier to perform without implying an invasive test for the patient.

Small amounts of free DNA circulate in both healthy and diseased human plasma or serum, and increased concentrations of plasma or serum DNA are present in cancer patients. The present inventors were the first to demonstrate that this DNA extracted from the plasma of cancer patients has tumor related characteristics. They include decreased strand stability, oncogene and tumor suppressor gene mutations, micro-satellite alterations, and gene hypermethylation. This has led to suggest that a non-invasive diagnostic test for cancer might be feasible using these molecular techniques.

Using essentially similar molecular techniques, tumor related mRNA have been detected in the plasma of cancer patients. These RNA markers are the result of an over expression of some genes in the cancer cells and may be found in increased quantities in the plasma/serum of cancer patients compared to healthy controls.

Now this over expression of genes is often accompanied by an amplification of the same gene in the cancer cells, and the present inventors have found that this amplification can be seen subsequently in the plasma/serum of the patient. It should be stressed that this amplification is independent of the fact that there is, as mentioned above, usually more plasma/serum DNA in cancer patients than in healthy controls.

The present inventors have therefore developed a cancer detection assay in plasma/serum measuring by adding and comparing the amount of DNA and RNA of certain genes in the plasma/serum of cancer patients that are the reflection of a gene amplification and a gene over expression. Thus gene amplification (seen by more DNA) and gene over expression (more RNA) are linked.

Consequently, the object of the present invention, reaching the above-mentioned aim, is consisting of a method for the diagnosis or the follow up of the evolution of cancers which comprises measuring together gene over expression (RNA) and gene amplification (DNA) in the bodily fluids of patients suspected to harbor cancer on any gene that is both amplified and over expressed in cancer cells and comparing to healthy controls.

More particularly, RNA and DNA are extracted from a bodily fluid, such as plasma, serum, sputum, saliva, etc, purified and amplified, and the over expressed RNA and amplified DNA are analyzed and compared to a unique house keeping gene.

As examples, the genes analyzed can be selected from hTERT, hTR, TEP1, MYCN, MYCC, ErbB2, Her2, Her2/Neu, Her1, Cyclin A and D1, ABL, SKP2, ETV6 (TEL-gene), MGC2177, PLAG1, PSMC6P and LYN.

Preferably, the nucleic acids are amplified by reversed transcriptase chain reaction (RT-PCR) and are analyzed by gel coloration, by radioactive immunological technique (RIA), by enzyme linked immunosorbant test (ELISA) or by a microchip test (gene array), and possibly quantified by any method for nucleic acid quantification.

The quantification of RNA and DNA can advantageously be carried out by real time PCR, such as "TAQMAN™", or on capillaries "LIGHTCYCLER™", or real time PCR and RT PCR of any company.

Furthermore, the genes analyzed may be compared to a reference nucleic acid extract (DNA and RNA) corresponding to the expression (RNA) and quantity (DNA) of a unique house keeping gene, or to a reference RNA corresponding to the expression of a house keeping coding gene, or to a reference DNA corresponding to a unique gene, or may be estimated in reference to a standard curve obtained with nucleic acids of a cell line.

In the following description of the present invention, telomerase RNA and DNA have been chosen as example, since telomerase activity is enhanced in 85 to 100% of cancers. But it must be stressed that the present invention is valid for all genes, and specially oncogenes that have been reported to be both amplified and over expressed in many cancers and cancer cell lines, for instance MYCN in neuroblastoma, ErbB2 in esophagal, breast and ovarian cancer, Her2, Her2/Neu and Her1 in breast and Her2/Neu in lung, Cyclin A an D1 in colorectal or laryngeal cancer, ABL in leukemias and lymphomas, SKP2 in non small cell lung cancer, ETV& (TEL-gene) in myelodysplastic syndrome. These are some of the most studied, but many others have been reported, such as MGC2177, PLAG1, PSMC6P, and LYN.

To illustrate the present invention, the hTERT gene was used, which codes for the reverse transcriptase of the telomerase ribonucleoprotein.

Telomerase is a ribonucleoprotein enzyme that synthesizes repeated telomeric sequences at chromosomal ends. The telomeres protect the chromosomal ends and at each cell division these telomeres are shortened. Telomerase composed of an RNA template (hTR) and a reverse transcriptase enzyme (hTERT) plus associated proteins such as TEP 1 that synthesizes these telomeres.

The activity of this enzyme has become an accepted indicator for the diagnosis and the prognosis of most malignant tumors. The expression of human telomerase RNA (hTR) or of the reverse transcriptase enzyme of the RNA telomerase (hTERT) or of the associated protein (TEP1) has been measured during the progression of several types of tumors. This has enabled the establishment of a correlation between this expression (the amount of RNA) and telomerase activity. Most cancers and immortalized cell lines have a high telomerase activity that reflects a mechanism that escapes normal aging regulations. We have a patent in Europe and a pending patent in the US for the measurement of the amount of mRNA in the plasma/serum coding for hTERT and TEP1.

Now, an amplification of the genes (DNA) coding for telomerase subunits (especially hTERT) has been observed in cancer cell lines and in different kinds of cancers. The present inventors have further observed an amplification of the hTERT gene in the plasma of cancer patients.

Although RNA components and mRNA coding for telomerase are cellular components, it was observed that, surprisingly, these components could be also found in an extracellular form in plasma or serum.

Indeed when both nucleic acids are extracted and amplified, the difference between the healthy controls and the cancer patients is surprisingly higher.

To sum up the method, the present inventors have shown an increased amount of hTR, hTERT and TEP1 RNA in the plasma or serum of persons suffering from breast, ovarian, head and neck, pancreatic, liver, stomach or colon cancer while these products have been shown to be absent in the blood of healthy persons. Moreover DNA coding for telomerase components in particular for hTERT can also be found in greater amounts (amplified) in the plasma of cancer patients than in healthy controls. It is known since a long time that there is often more DNA in the plasma of cancer patients than in the plasma of healthy controls (this has been demonstrated by measuring the amount of beta-globin for instance), but hTERT DNA yields even more than what could be expected, giving evidence of an amplification of this gene.

More precisely, the method of diagnosis according to the invention consists in extracting the nucleic acids (RNA and DNA) from the plasma or the serum of the blood, purifying it and amplifying it in order to establish the presence and the quantity of the product made in this case by the of components hTERT. This shall be done in a comparative manner between the plasma or serum of a person suspected of malignancy and the plasma or serum of a healthy person or of a control suffering from a non-malignant disease.

The amplification product of the DNA and of the RNA components transcribed into DNA by RT-PCR are detected and quantified. This can be done by any nucleic acid quantification method.

Similarly, any technique of extraction of purification and of amplification of the nucleic acids (DNA and RNA) in the plasma or the serum may be used.

The present invention will now be illustrated in a non-limitative manner by the following example related to the diagnosis of some cancers using hTERT DNA and RNA quantification.

EXAMPLE

Diagnosis of different cancers by the detection of amplified hTERT DNA and over exypressed hTERT RNA in the plasma or serum of the blood.

Blood samples (2 ml) were collected in EDTA tubes prior to surgery or treatment on patients bearing small malignant breast tumors or on patients suffering of head and neck, colorectal, pancreatic and liver cancer. Blood was taken in the same way as healthy volunteers for controls.

To guarantee good quality plasma nucleic acids, the whole blood samples should be centrifuged as soon as possible. If the centrifugation cannot take place immediately, the blood samples should be stored at 4° immediately after blood collection and centrifuged within 6 hours. The blood samples at 1,600 g for 10 min at 4° C. The plasma was transferred into new tubes taking care not to disturb the buffy coat layer. A second round centrifugation of the plasma was performed at 16,000 g for 10 min at 4° C. The plasma was finally transferred into new tubes taking care not to disturb the underlying cell pellet and stored if necessary at −70°.

RNA and DNA were extracted using a commercially available kit (Ultrasens viral kit from Qiagen), which extracts DNA as well as RNA, according to manufacturers instructions.

The primers and TAQMAN™ probe for hTERT were located on one exon and which would yield both RNA and DNA:

```
F: 5'-ACC GTC TGC GTG AGG AGA TC-3';
(SEQ ID NO: 1)

R: 5'-CCG GTA GAA AAA AGA GCC TGT TC-3'
(SEQ ID NO: 2)

and the PROBE
5'Fam -TGT ACG TCG TCG AGC TGC TCA GGT CTT T-3'
TAMRA (SEQ ID NO: 3).
```

As reference for RNA and DNA we used the beta-Globin gene on exon 2: forward primer: 5' CTGCTGGTGGTC-TACCCTTG 3' (SEQ ID NO: 4); Reverse primer: 5' CCT-GAAGTTCTCAGGATCCA 3' (SEQ ID NO: 5); and Hybridization probe:5'Fam. CTCCTGATGCTGT-TATGGGCAACCCT 3 TAMRA' (SEQ ID NO: 6) which would yield both RNA and DNA or the GAPDH gene on exon 8: Forward primer 5'GTGGACCTGACCTGCCG3' (SEQ ID NO: 7); Reverse primer 5' GGAG-GAGTGGGTGTCGC 3' (SEQ ID NO: 8) and the probe for TAQMAN™ 5' FAM-AAGGGCATCCTGGGCTACACT-GAGCA3' TAMRA (SEQ ID NO: 9).

These reference primers for RNA and DNA can be replaced by any housekeeping unique gene. The results given below were calculated using arbitrary quantities expressed either as CT (cycle threshold numbers) or $2^{\Delta CT}$ values (for instance $2^{CT}$ of hTERT$^{-CT}$ of b-Globin). They always compared extractions of plasma nucleic acids of cancer patients and healthy donors extracted the same day and with the same amount (0.5 ml) of plasma/serum. It is possible to estimate in another way by comparing the results to a curve obtained by known quantities of one gene.

The QuantiTect Probe RT-PCR (Qiagen) was used in 25 μl RT-PCR reaction mixture containing the manufacturer's Master Mix, the RT mix (Omniscript™ reverse transcriptase, Sensiscript™ reverse transcriptase, hot-start Taq™ DNA polymerase) to which we added the set of primers (0.4 μM) and TAQMAN™ probe (0.1 μM) and 3 to 6 μl of the 30 μl of eluted nucleic acids. The RT-PCT conditions of the mixture were an initial incubation at 50° C. for 30 min followed by a 95° C. incubation for 15 min to activate the HotstarTaq™ DNA Polymerase, then 50 cycles at 94° C. (15 sec), 60° C. (1 min).

All base sequences mentioned here above as primer examples are known and may as such be consulted on the web site of the Genome Database. They may be replaced by other primers and probes located on the above-mentioned genes. Reference genes may be changed by other genes.

Results Obtained:

Data have been obtained on 74 cancer patients and 51 controls with 98% specificity. The sensitivity changes from cancer to cancer ranging from 81% to over 90%. The cancer patients suffered from head and neck, breast, colorectal, pancreatic and liver cancers.

The results obtained by Real Time Quantitative RT PCR measuring both DNA and RNA of hTERT compared to beta-Globin gene in the plasma of cancer patients and healthy controls are presented on the following Table.

| Samples studied | Number of samples | hTERT positive % |
|---|---|---|
| CONTROLS | 51 | 2% |
| PANCREATIC CANCER | 27 | 81% |

-continued

| Samples studied | Number of samples | hTERT positive % |
|---|---|---|
| HEAD AND NECK | 16 | 94% |
| COLORECTAL | 18 | 83% |
| BREAST | 7 | 100% |
| LIVER | 6 | 83% |

Furthermore, the results obtained are illustrated on the annexed figures, where;

Figure 1:
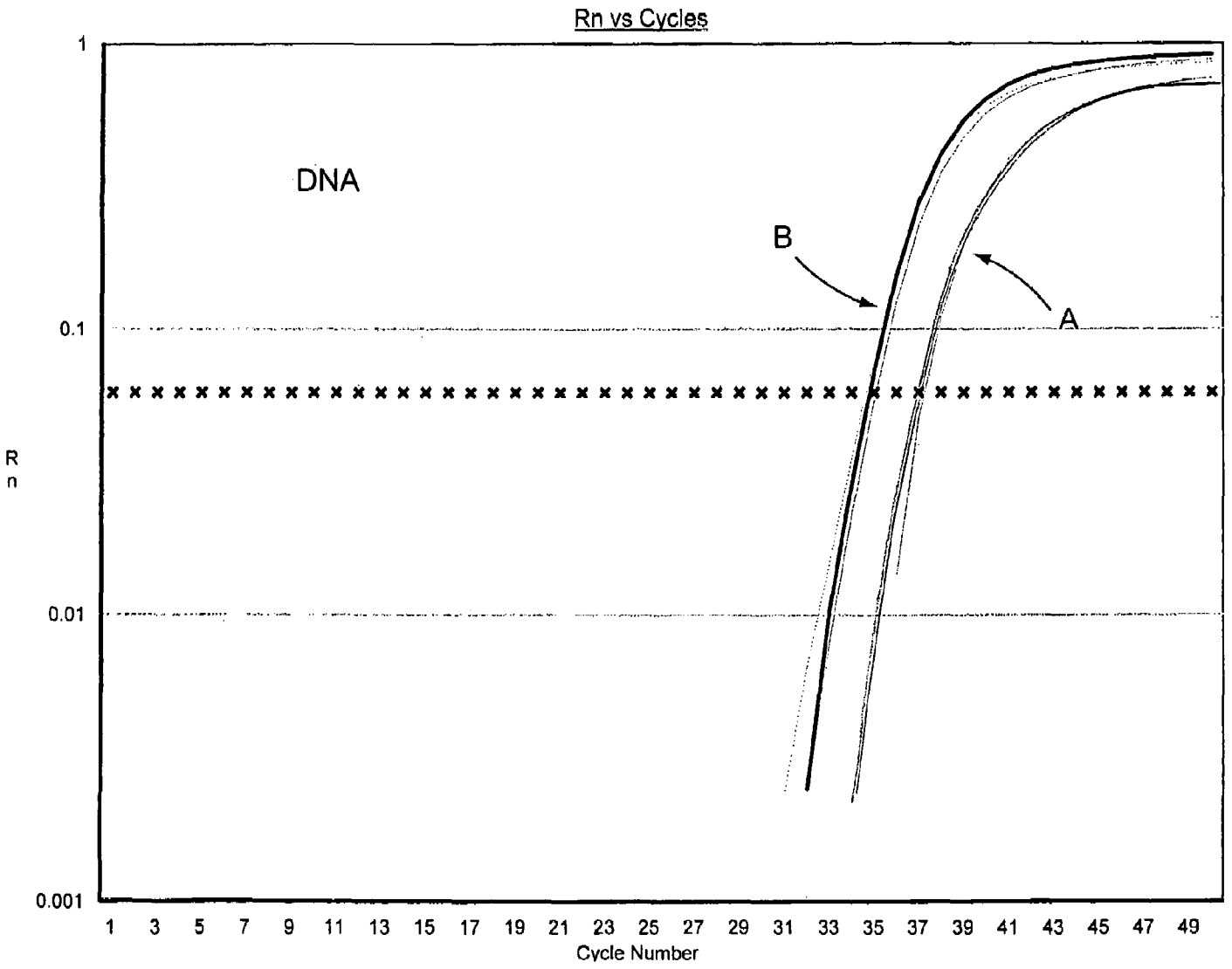
FIG. 1 shows as reference the amplification plots obtained using real time quantitative PCR for the hTERT gene (DNA), and with the x-axis being the cycle number of the PCR reaction and the y-axis the fluorescence intensity over background.

As it can easily be seen on FIG. 1, the first group of lines (A) with a CT value around 37 is composed of the amplification product of samples of DNA from healthy donors with hTERT primers, and the second group (B) with a CT value around 35 is composed of the amplification product of samples of plasma DNA from patients suffering from head and neck cancer.

Figure 2:
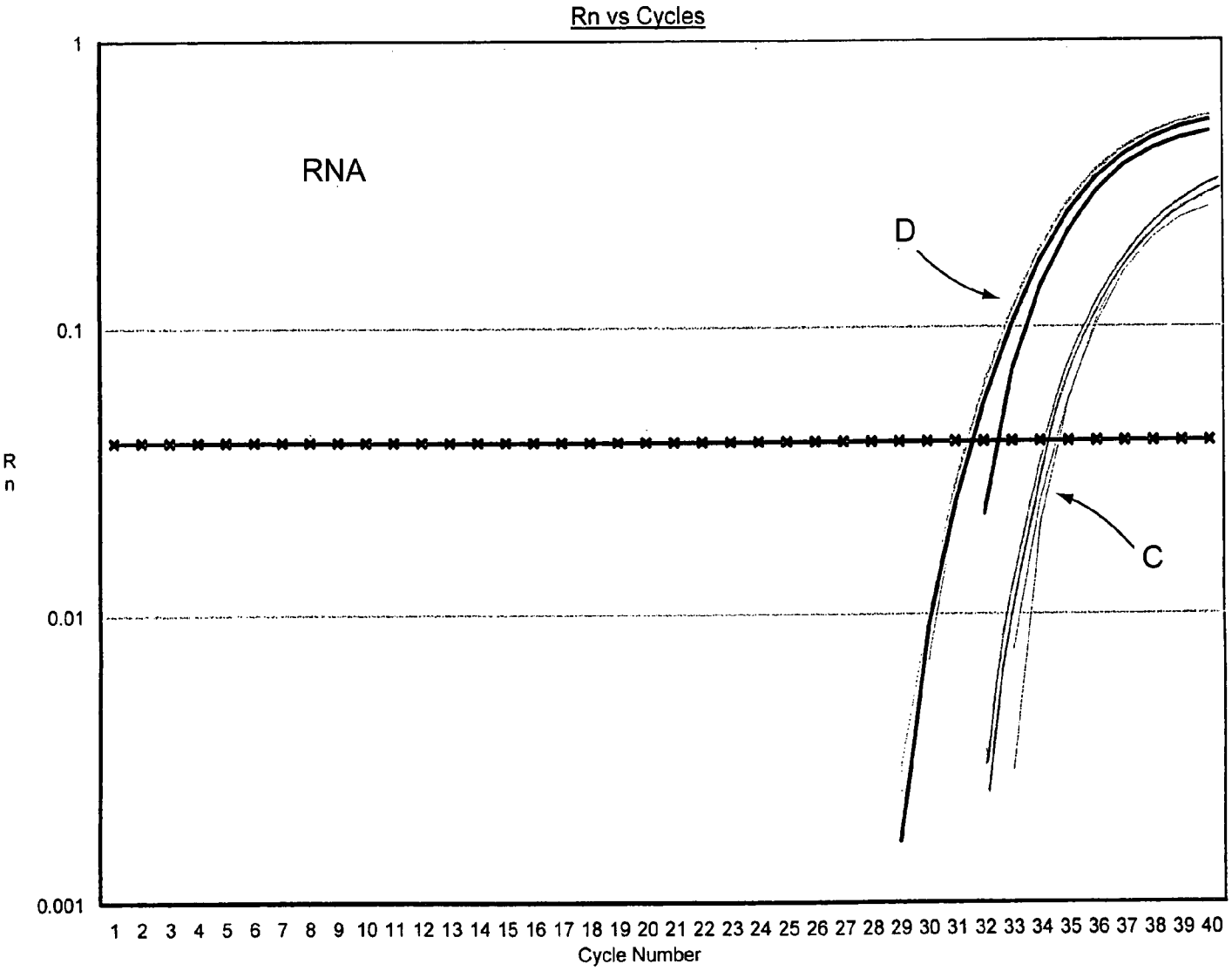
FIG. 2 shows as reference the amplification plots obtained using real time quantitative RT-PCR for the hTERT gene (RNA), and with the x-axis being the cycle number of the PCR reaction and the y-axis the fluorescence intensity over background.

On FIG. 2, the first group of lines (C) with a CT value around 34 is composed of the amplification product of samples of RNA from healthy donors with hTERT primers, and the second group (D) with a CT value around 32 is composed of the amplification product of samples of plasma RNA from patients suffering from head and neck cancer. A difference of 2 CT values represents a difference of 4 times RNA values obtained from the same amount of plasma.

Figure 3:
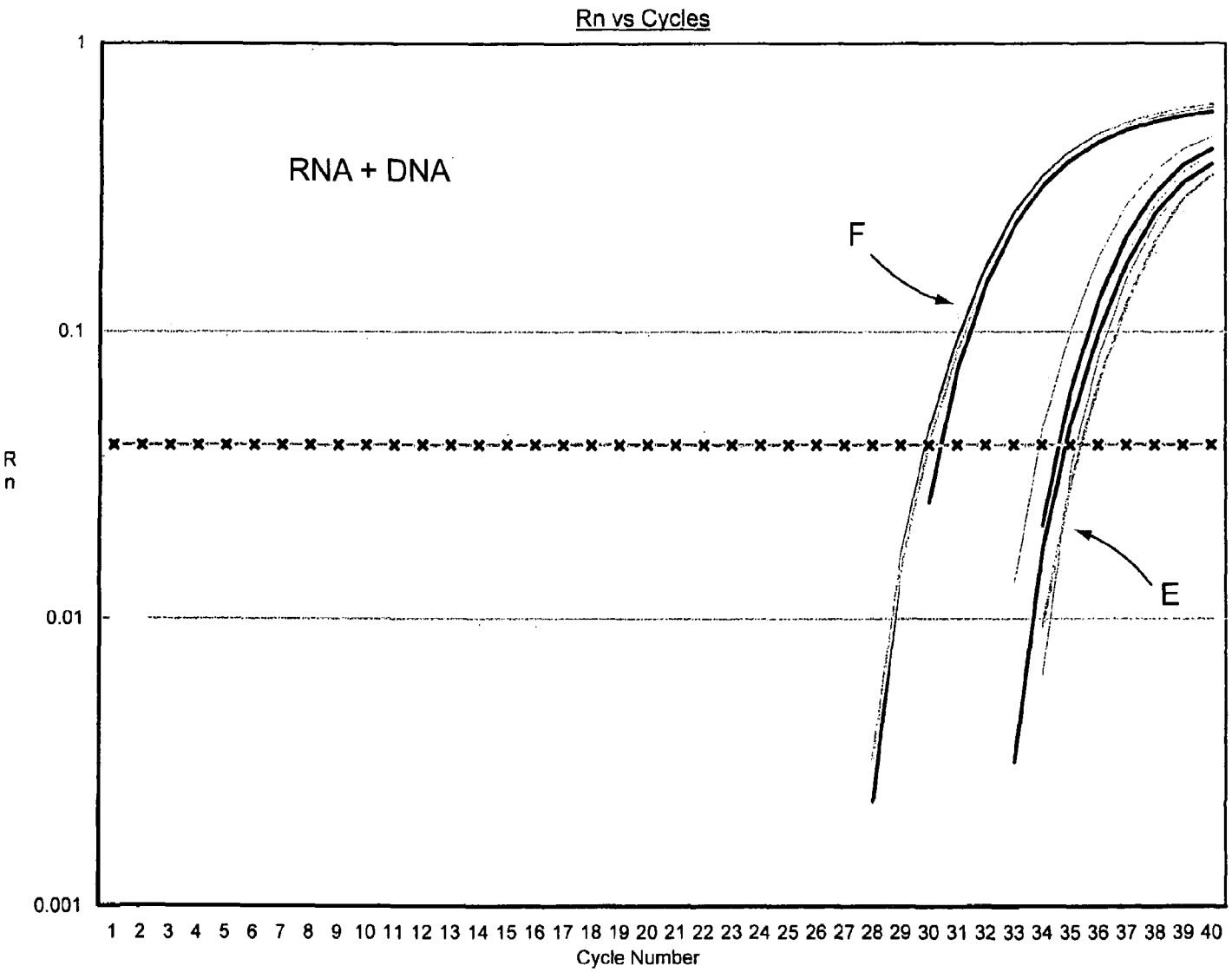
FIG. 3 shows the amplification plots obtained using real time quantitative RT-PCR for the hTERT gene (total nucleic acids DNA and RNA), according to the present invention, and with the x-axis being the cycle number of the PCR reaction and the y-axis the fluorescence intensity over background.

On FIG. 3, which represents the results the first group of lines (E) with a CT value around 35 is composed of the amplification product of samples of plasma nucleic acid from healthy donors with hTERT primers, and the second group (F) with a CT value around 29 is composed of the amplification product of samples of plasma nucleic acid from patients suffering from head and neck cancer. The difference between the CT values (comprising RNA and DNA) of the control group and the cancer group is higher than in FIGS. 1 and 2, DNA or RNA are measured. This demonstrates the clear advantage of the method according to the present invention.

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
```

<223> OTHER INFORMATION: Description of Artificial Sequence: Synthetic
primer

<400> SEQUENCE: 1 accgtctgcg tgaggagatc 20

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 2 ccggtagaaa aaagagcctg ttc 23

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
probe

<400> SEQUENCE: 3 tgtacgtcgt cgagctgctc aggtcttt 28

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 4 ctgctggtgg tctacccttg 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 5 cctgaagttc tcaggatcca 20

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
probe

<400> SEQUENCE: 6 ctcctgatgc tgttatgggc aaccct 26

<210> SEQ ID NO 7
<211> LENGTH: 17
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 7

gtggacctga cctgccg                                                    17


<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

ggaggagtgg gtgtcgc                                                    17


<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9

aagggcatcc tgggctacac tgagca                                          26
```

The invention claimed is:

[1. A method for the diagnosis or the follow up of the evolution of cancers which comprises measuring both gene over-expression (RNA) and gene amplification (DNA) of a gene present in the bodily fluids of a patient that is both amplified and over-expressed in cancer cells and comparing to healthy controls.]

[2. The method according to claim 1, wherein RNA and DNA are extracted from a bodily fluid, purified and amplified, and the over-expressed RNA and amplified DNA are analyzed and compared to a house keeping gene.]

[3. The method according to claim 2, wherein the genes analyzed are selected from hTERT, hTR, TEP1, MYCN, MYCC, ErbB2, Her2, Her2/Neu, Her 1, Cyclin A and D1, ABL, SKP2, ETV6 (TELgene), MGC2177, PLAG1, PSMC6P and LYN.]

[4. The method according to claim 2, wherein the nucleic acids are amplified by reverse transcriptase chain reaction (RT-PCR).]

[5. The method according to claim 3, wherein the nucleic acids are amplified by reverse transcriptase chain reaction (RT-PCR).]

[6. The method according to claim 1, wherein the genes analyzed are selected from the group consisting of hTERT, hTR, TEP1, MYCN, MYCC, ErbB2, Her2, Her2/Neu, Her 1, Cyclin A and D1, ABL, SKP2, ETV6 (TELgene), MGC2177, PLAG1, PSMC6P and LYN.]

[7. The method according to claim 6, wherein the nucleic acids are amplified by reverse transcriptase chain reaction (RT-PCR).]

[8. The method according to claim 1, wherein the nucleic acids are amplified by reverse transcriptase chain reaction (RT-PCR).]

[9. The method according to claim 1, wherein the genes analyzed are compared to a reference nucleic acid extract (DNA and RNA) corresponding to the expression (RNA) and quantity (DNA) of a house keeping gene.]

[10. The method according to claim 1, wherein the genes analyzed are compared to a reference RNA corresponding to the expression of a house keeping gene.]

[11. The method according to claim 1, wherein the genes analyzed are compared to a reference DNA corresponding to a housekeeping gene.]

[12. The method according to claim 1, wherein the gene quantification may be estimated in reference to a standard curve obtained with nucleic acids of a cell line.]

[13. The method according to claim 1, wherein the nucleic acids RNA and DNA are analyzed by gel coloration, by radioactive immunological technique (RIA), by enzyme linked immunosorbant test (ELISA) or by a microchip test (gene array), and quantified by any method for nucleic acid quantification.]

[14. The method according to claim 1, wherein the nucleic acids RNA and DNA are quantified by real time RT PCR.]

[15. The method according to claim 1, wherein the RNA and DNA are extracted from the patient and measured simultaneously.]

[16. A method for measuring both gene over-expression (RNA) and gene amplification (DNA) in a patient suspected of having cancer, wherein the gene is selected from the group consisting of hTERT, hTR, TEP1, MYCN, MYCC, ErbB2, Her2, Her2/Neu, Her 1, Cyclin A, Cyclin D1, ABL, SKP2, ETV6 (TELgene), MGC2177, PLAG1, PSMC6P and LYN, comprising:

obtaining a sample of a bodily fluid from a patient, and extracting both RNA and DNA simultaneously from said sample, measuring both gene over-expression (RNA) and gene amplification (DNA) at the same time in said sample, and comparing said measurement to a healthy control.]

[17. The method according to claim 16, wherein RNA and DNA are extracted from a bodily fluid, purified and amplified, and the over-expressed RNA and amplified DNA are analyzed and compared to a house keeping gene.]

[18. The method according to claim 17, wherein the over-expressed and amplified gene is hTERT.]

[19. The method according to claim 18, wherein the nucleic acids are amplified by reverse transcriptase chain reaction (RT-PCR).]

[20. The method according to claim 16, wherein the genes analyzed are compared to a reference nucleic acid extract (DNA and RNA) corresponding to the expression (RNA) and quantity (DNA) of a house keeping gene.]

[21. The method according to claim 16, wherein the genes analyzed are compared to a reference RNA corresponding to the expression of a house keeping gene.]

*22. A method for detecting gene amplification of one or more genes that occurs in cancer cells of a subject having cancer, the gene amplification of the one or more genes being indicative of cancer, the method comprising:*

*(i) obtaining a blood sample from the subject;*

*(ii) separating cell-free deoxyribonucleic acid (DNA) from a plasma or serum fraction of the blood sample;*

*(iii) amplifying DNA of the one or more genes of the subject present in the cell-free DNA separated from the plasma or serum fraction;*

*(iv) amplifying DNA of a reference gene present in the cell-free DNA separated from the plasma or the serum fraction;*

*(v) measuring amounts of the amplified DNA of the one or more genes;*

*(vi) measuring an amount of the amplified DNA of the reference gene, wherein the reference gene is different than the one or more genes;*

*(vii) determining if the amounts of the amplified DNA of the one or more genes are increased relative to the amount of amplified DNA of the reference gene; and*

*(viii) detecting the gene amplification in cancer cells of the one or more genes if the amounts of the amplified DNA of the one or more genes are determined to be increased relative to the amount of amplified DNA of the reference gene.*

*23. The method according to claim 22, wherein the one or more genes are a plurality of genes.*

*24. The method according to claim 22, wherein the one or more genes include oncogenes.*

*25. The method according to claim 22, further comprising detecting a tumor-related characteristic in the one or more genes present in the plasma or serum fraction.*

*26. The method according to claim 22, wherein the separating comprises extracting cell-free DNA from the plasma or serum fraction.*

*27. The method according to claim 26, further comprising amplifying DNA of the one or more genes of the extracted cell-free DNA.*

*28. The method according to claim 27, wherein the amplifying comprises using polymerase chain reaction.*

*29. The method according to claim 22, wherein the one or more genes are selected from the group consisting of hTERT, hTR, TEPI, MYCN, MYCC, ErbB2, Her2, Her2/Neu, Her1, Cyclin A and D1, ABL, SKP2, ETV6 (TELgene), MGC2177, PLAG!, PSMC6P and LYN.*

*30. The method according to claim 22, wherein the cancer is neuroblastoma, and wherein the one or more genes include MYCN.*

*31. The method according to claim 22, wherein the cancer is selected from the group consisting of esophageal cancer, breast cancer, and ovarian cancer, and wherein the one or more genes include ErbB2.*

*32. The method according to claim 22, wherein the cancer is breast cancer or lung cancer, and wherein the one or more genes are selected from the group consisting of: Her2, Her2/Neu, and Her1.*

*33. The method according to claim 22, wherein the cancer is colorectal cancer or laryngeal cancer, and wherein the one or more genes include Cyclin A or Cyclin D1.*

*34. The method according to claim 22, wherein the cancer is selected from the group consisting of: leukemia and lymphoma, and wherein the one or more genes include ABL.*

*35. The method according to claim 22, wherein the cancer is non-small cell lung cancer, and wherein the one or more genes include SKP2.*

*36. The method according to claim 22, wherein the cancer is myelodysplastic syndrome, and wherein the one or more genes include ETV6.*

*37. The method according to claim 22, wherein the cancer is selected from the group consisting of breast cancer, ovarian cancer, head and neck cancer, pancreatic cancer, liver cancer, stomach cancer, and colorectal cancer, and wherein the one or more genes include hTR, hTERT, or TEPI.*

*38. The method according to claim 22, wherein the cancer is nasopharyngeal cancer, and wherein the one or more genes is not Epstein Barr Virus DNA.*

*39. The method according to claim 22, further comprising following up with the subject based on the presence of the gene amplification.*

* * * * *